United States Patent
Prasad et al.

(10) Patent No.: US 6,274,550 B1
(45) Date of Patent: Aug. 14, 2001

(54) AZAFTIG, A PROTEOGLYCAN FOR MONITORING CACHEXIA AND FOR CONTROL OF OBESITY

(75) Inventors: Chandan Prasad; Julio E. Figueroa, II, both of New Orleans; Parakat Vijayagopal, Kenner, all of LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 09/340,873

(22) Filed: Jun. 28, 1999

Related U.S. Application Data

(63) Continuation of application No. 09/107,756, filed on Jun. 30, 1998, now abandoned
(60) Provisional application No. 60/150,695, filed on Jun. 30, 1998.

(51) Int. Cl.[7] .................................................. A61K 38/16
(52) U.S. Cl. .............................. 514/8; 424/520; 424/545; 530/395; 530/397
(58) Field of Search .................................. 530/395, 397; 514/8; 424/520, 545

(56) References Cited

PUBLICATIONS

Kolset et al. "Proteoglykaner og patologi–nye aspekter" [Proteoglycans and Pathology–New Aspects], Tidskrift For Den Norske Laegeforening, vol. 117, No. 7 (Mar. 10, 1997), pp. 951–4. (Abstract only).

R.B. Verdery, "Reversible and irreversible weight loss (cachexia) in the elderly," Textbook of Internal Medicine, 2d Edition (V.T. DeVita et al. eds.), Ch. 523, pp. 2424–2425 (1992).

K.I. Marton, "Approach to patient with unintentional weight loss," Textbook of Internal Medicine, 2d Edition (V.T. DeVita et al. eds.), Ch. 444, pp. 2113–2115 (1992).

R. M. Jordan et al., "Weight loss," in Internal Medicine, 4th Edition (J.H. Stein ed.), Ch. 152, pp. 1260–1262 (1994).

C.P. Artz et al., "Burns: Including cold, chemical, and electrical injuries," Textbook of Surgery, 11th Edition (D.C. Sabiston, Jr. ed.), Ch. 15, pp 295–322 1997).

E. Braunwald, "Heart Failure," Harrison's Principles of Internal Medicine, 13th Edition (K.J. Isselbacher ed.), Ch. 195, pp. 998–1009 (1994).

D.W. Foster, "Gain and loss in weight," in Harrison's Principles of Internal Medicine, 13th Edition (K.J. Isselbacher ed.), Ch. 40, pp. 221–223 (1994).

G.O. Coodley et al., "The HIV Wasting Syndrome: a Review," Journal of Acquired Immune Deficiency Syndromes, vol. 7, pp. 681–694 (1994).

L.M. Hecker et al., "Malnutrition in patients with AIDS," Nutrition Reviews, vol. 48, pp. 393–401 (1990).

N.M. Graham et al., "Clinical factors associated with weight loss related to infection with Human Immunodeficiency Virus Type 1 in the multicenter AIDS cohort study," American Journal of Epidemiology, vol. 137, pp. 439–46 (1993).

K.A. Nelson et al., "The cancer anorexia–cachexia syndrome," Journal of Clinical Oncology, vol. 12, pp. 213–25 (1994).

Grunfeld et al., "Metabolic disturbance and wasting in the acquired immunodeficiency syndrome," The New England Journal of Medicine, vol. 327, pp. 329–337 (1992).

S.A. Lieberman et al., "Anabolic effects of recombinant insulin–like growth factor–I in cachectic patients with the acquired immunodeficiency syndrome," Journal of Clincal Endocrinology and Metabolism, vol. 78, pp. 404–410 (1994).

J. Knoll, "Satietin, a blood–borne, highly selective and potent anorectic glycoprotein," Biomed. Biochim. Acta, vol. 44, pp. 317–328 (1985).

J. Knoll, "Satietin: a 50,000 Dalton glycoprotein in human serum with potent, long–lasting and selective anorectic activity," J. Neural Transmission, vol. 59, pp. 163–194 (1984).

R.K. Upreti et al., "A step towards developing the expertise to control hunger and satiety: Regulatory role of satiomem—A membrane proteoglycan," Neurochemical Research, vol. 20, pp. 375–384 (1995).

A.M. Kidwai et al., "A Novel Plant membrane proteoglycan which causes anorexia in animals," Molecular and Cellular Biochemistry, vol. 120, pp. 111–117 (1993).

A.M. Kidwai et al., "Isolation of an anorexigenic protein from membranes," Molecular and Cellular Biochemistry, vol. 91, pp. 117–122 (1989).

P.T. Todorov et al., "Structural Analysis of a Tumor–produced Sulfated Glycoprotein Capable of Initiating Muscle Protein Degradation," The Journal of Biological Chemistry, vol. 272, pp. 12279–88 (1997).

P. Cariuk et al., "Induction of Cachexia in Mice by a Product isolated from the urine of cachectic cancer patients," British Journal of Cancer, vol. 76, pp. 606–613 (1997).

M.J. Lorite et al., "Induction of muscle protein degradation by a tumour factor," British Journal of Cancer, vol. 76, pp. 1035–1040 (1997).

(List continued on next page.)

*Primary Examiner*—Jeffrey Stucker
(74) *Attorney, Agent, or Firm*—Bonnie J. Davis; John H. Runnels

(57) ABSTRACT

A proteoglycan ("azaftig") with a molecular weight of approximately 24,000 Dalton has been isolated and partially characterized from the urine of cachectic cancer and non-cancer patients. Azaftig has been shown to bind to receptors on fat cell membranes, and to cause lipolysis. Azaftig does not bind to muscle cell membranes, or cause proteolysis in muscle tissue. Azaftig detection in urine or other body fluids will allow early identification of patients in which weight loss may become a problem. Azaftig may also aid fat loss in humans in which obesity is a threat to health.

3 Claims, 17 Drawing Sheets

OTHER PUBLICATIONS

P. Todorov et al., "Characterization of a cancer cachectic factor," Nature, vol. 379, pp. 739–742 (1996).

P.T. Todorov et al., "Induction of muscle protein degradation and weight loss by a tumor product," Cancer Research, vol. 56, pp. 1256–1261 (1996).

T.M. McDevitt et al., "Purification and Characterization of a Lipid–mobilizing Factor Associated with Cachexia–inducing Tumors in Mice and Humans," Cancer Research, vol. 55, pp. 1458–63 (1995).

J.E. Belizario et al., "Bioactivity of skeletal muscle proteolysis–inducing factors in the plasma proteins from cancer patients with weight loss," British Journal of Cancer, vol. 63, pp. 705–710 (1991).

S.A. Beck et al., "Lipid mobilising factors specifically associated with cancer cachexia," British Journal of Cancer, vol. 63, pp. 846–850 (1991).

P. Groundwater et al., "Alteration of serum and urinary lipolytic activity with weight loss in cachectic cancer patients," British Journal of Cancer, vol. 62, pp. 816–821 (1990).

S.A. Beck et al., "Alterations in serum lipolytic activity of cancer patients with response to therapy," British Journal of Cancer, vol. 62, pp. 822–825 (19910).

F.X. Pi–Sunyer, "Medical Hazards of Obesity," Annals of Internal Medicine, vol. 119, pp. 655–660 (1993).

G.A. Bray, "Pathophysiology of Obesity," American Journal of Clinical Nutrition, vol. 55, pp. 488S–494S (1992).

J. Figueroa et al., "Abundance of a 24 KD proteoglycan in the urine of both cachectic AIDS and cachectic cancer patients," submitted for publication to AIDS Research and Human Retroviruses (1998).

J. Figueroa et al., "Azaftig, a urinary proteoglycan from cachectic cancer patients, causes profound weight loss in mice," submitted for publication in Life Sciences (1998).

Kosel et al. "Proteoglykaner og patologi—nye asperkter" [Proteoglycans and Pathology—New Aspects], Tidsskrift for Den Norske Laegeforening, vol. 117, No. 7 (Mar 10, 1997), pp. 951–4.*

* cited by examiner

AZAFTIG, A PROTEOGLYCAN FOR MONITORING CACHEXIA AND FOR CONTROL OF OBESITY

The benefit of the Jun. 30, 1998 filing date of provisional application 60/150,695 (which was a continuation of non-provisional application 09/107,756 filed Jun. 30, 1998 now abandoned) is claimed under 35 U.S.C. §119(e).

This invention pertains to the detection of a propensity for cachexia and to the control of obesity.

Cachexia is defined as significant weight loss. It occurs commonly in cancer patients and HIV-infected individuals, but can also be caused by hypercatabolism due to cardiac failure (especially, right-sided or biventricular failure), hepatic failure, renal failure, burns, inflammation (including sepsis), infection or tuberculosis. See R. B. Verdery, "Reversible and irreversible weight loss (cachexia) in the elderly," in Textbook of Internal Medicine, 2d Edition (V. T. DeVita et at. eds.), Ch. 523, pp. 2424–2425 (1992); K. I. Marton, "Approach to patient with unintentional weight loss," in Textbook of Internal Medicine, 2d Edition (V. T. DeVita et al. eds.), Ch. 444, pp. 2113–2115 (1992); R. M. Jordan et al., "Weight loss," in Internal Medicine, 4th Edition (J. H. Stein ed.), Ch. 152, pp. 1260–1262 (1994); C. P. Artz et al., "Burns: Including cold, chemical, and electrical injuries," in Textbook of Surgery, 11th Edition (D. C. Sabiston, Jr. ed.), Ch. 15, pp. 295–322 (1977); E. Braunwald, "Heart Failure," in Harrison's Principles of Internal Medicine, 13th Edition (K. J. Isselbacher ed.), Ch. 195, pp. 998–1009 (1994); and D. W. Foster, "Gain and loss in weight," in Harrison's Principles of Internal Medicine, 13th Edition (K. J. Isselbacher ed.), Ch. 40, pp. 221–223 (1994). Over 50% of cancer and HIV-infected patients experience an unintended weight loss of greater than 10% of their baseline weight. Moreover, this weight loss is associated with an increase in morbidity and mortality. Many cachectic patients manifest multiple physiological problems involving the immune system, muscular system, and hepatic function that can be directly related to loss of body weight or wasting. Therefore, understanding the mechanisms of cachexia in patients can lead to better treatment and consequently can have a substantial impact on the quality of life and survival of many cancer and HIV/AIDS patients. See G. O. Coodley et al., "The HIV Wasting Syndrome: a Review," Journal of Acquired Immune Deficiency Syndromes, vol. 7, pp. 681–694 (1994); L. M. Hecker et al., "Malnutrition in patients with AIDS," Nutrition Reviews, vol. 48, pp. 393–401 (1990); N. M. Graham et al., "Clinical factors associated with weight loss related to infection with Human Immunodeficiency Virus Type 1 in the multicenter AIDS cohort study," American Journal of Epidemiology, vol. 137, pp. 439–46 (1993); and K. A. Nelson et al., "The cancer anorexia-cachexia syndrome," Journal of Clinical Oncology, vol. 12, pp. 213–25 (1994).

Despite the prevalence of weight loss in cancer patients, the mechanisms underlying the weight loss are unknown. Current explanations for cancer or AIDS-associated weight loss are divided into two general categories—(1) mechanisms that decrease food intake (anorexia); and (2) mechanisms that increase energy expenditure through altered or increased metabolism. Hecker et al., 1990. Any mismatch between energy intake and expenditure will result in a change in weight.

Many cancer or AIDS patients have decreased oral intake and, therefore, decreased energy consumption. Accordingly, despite normal or even decreased energy expenditures in these patients, they may lose weight. Other patients experience anorexia due to the cancerous tumor itself (either by a mechanical obstruction or a change in tissue function) or due to the therapy used to treat the tumor, e.g., chemotherapy. Graham et al., 1993; Nelson et al., 1994. Similarly, many HIV/AIDS patients experience significant weight loss that correlates with decreased caloric intake. See C. Grunfeld et al., "Metabolic disturbance and wasting in the acquired immunodeficiency syndrome," The New England Journal of Medicine, vol. 327, pp. 329–337 (1992). Thus, anorexia plays a major role in weight loss for the majority of both cancer and HIV/AIDS patients.

Factors that have been identified as causing anorexia in patients include opportunistic gastrointestinal infections or tumors, side effects of treatment, enteropathy, central nervous system disease, and psychiatric disorders. In addition, numerous physiological mediators of anorexia have been reported in the literature, including tumor necrosis factor, interleukin-1, interleukin-6, $\gamma$-interferon, and $\alpha$-interferon. Coodley et al., 1994; Nelson et al., 1994; and Grunfeld et al., 1990. Yet the mechanisms by which these or other mediators induce anorexia remain unknown.

Another proposed mechanism contributing to the weight loss seen in cancer or AIDS patients is an increased or ineffective metabolism. It has been reported, and disputed, that resting energy expenditures in some patients rise throughout the course of the disease and increase even more at the end stage. See Coodley et al., 1994; Nelson et al., 1994; and Grunfeld et al., 1990. However, alterations in resting or total energy expenditures do not correlate with weight loss. Therefore, it is unlikely that increased energy demands alone account for wasting.

Even with decreased energy use, patients may lose weight due to ineffective metabolism. It is hypothesized that during episodes of weight loss, patients fail to switch from carbohydrate and protein oxidation to the fatty acid oxidation that would normally occur under conditions of starvation. This failure explains the observation that patients lose predominantly muscle mass rather than fat tissue. It has also been suggested that futile cycling of lipid metabolism can waste energy, thus accelerating the necessity of carbohydrate and protein breakdown, despite a decrease in total energy expenditure. See Coodley et al., 1994; Nelson et al., 1994; and Grunfeld et al., 1990.

Recently, alterations in hormone metabolism have been proposed as possible etiologies of HIV/AIDS or cancer-related weight loss, particularly due to muscle wasting. During severe or chronic infections, patients, particularly HIV/AIDS patients, demonstrate resistance to the actions of growth hormone. Because growth hormone acts to maintain muscle mass, it has been hypothesized that this resistance leads to muscle wasting and weight loss in HIV/AIDS patients. Recently, researchers demonstrated that HIV/AIDS patients with the wasting syndrome have a decreased response to exogenous growth hormone compared with a control group. In particular, the effects of growth hormone on insulin-like growth factor-I (IGF-I, a major mediator of growth hormone action) secretion was studied. When IGF-I was exogenously administered to patients with the wasting syndrome, the patients experienced a transient increase in nitrogen retention, but returned to baseline after 8–10 days. See S. A. Lieberman et al., "Anabolic effects of recombinant insulin-like growth factor-I in cachectic patients with the acquired immunodeficiency syndrome," Journal of Clinical Endocrinology and Metabolism, vol. 78, pp. 404–410 (1994). Thus, alterations in the growth hormone/IGF-I system may play an important role in HIV/AIDS cachexia.

In cancer patients, growth hormone resistance has been seen, but also other important hormones, including insulin and its antagonist glucagon, appear to be abnormally produced. Since these hormones are essential to normal metabolism, it has been postulated that abnormalities in these pathways explain the wasting syndrome in these patients. See Nelson et al., 1994. Unfortunately, the mechanisms by which cancer or HIV infection causes these alterations in hormone metabolism are poorly understood at best.

The control of caloric intake and body weight maintenance is very complex. The search for endogenous mediators over several decades has led to the identification of a variety of substances ranging from simple amino acids to large proteins and glycoproteins. However, it has been difficult to establish an unequivocal association between the amount of any one of these factors and human disease states such as anorexia/cachexia and anorexia nervosa.

Three glycoproteins or proteoglycans that modulate appetite or body weight have been identified: satietin, satiomem, and MAC16 mouse protein. A glycoprotein is a protein that contains attached carbohydrates that are not polymers of repeating units. In contrast, a proteoglycan is a protein that contains repeating units of glycosaminoglycans covalently attached to a core protein.

Satietin is a glycoprotein with a molecular weight of 50,000 Dalton that has been isolated from human and animal sera. Satietin is known to suppress food intake in mammals. See J. Knoll, "Satietin, a blood-borne, highly selective and potent anorectic glycoprotein," Biomed. Biochim. Acta, vol. 44, pp. 317–328 (1985); and J. Knoll, "Satietin: a 50,000 Dalton glycoprotein in human serum with potent, long-lasting and selective anorectic activity," J. Neural Transmission, vol. 59, pp. 163–194 (1984).

Satiomem is a proteoglycan with a molecular weight of 50,000 Dalton that has been isolated from plant and animal membranes, including human erythrocyte membrane. Satiomem has been shown to suppress food intake and cause weight loss. See R. K. Upreti et al., "A step towards developing the expertise to control hunger and satiety: Regulatory role of satiomem—A membrane proteoglycan," Neurochemical Research, vol. 20, pp. 375–384 (1995); A. M. Kidwai et al., "A Novel Plant membrane proteoglycan which causes anorexia in animals," Molecular and Cellular Biochemistry, vol. 120, pp. 111–117 (1993); and A. M. Kidwai et al., "Isolation of an anorexigenic protein from membranes," Molecular and Cellular Biochemistry, vol. 91, pp. 117–122 (1989).

The MAC16 protein is a sulfated, phosphated glycoprotein of 24 kDa initially identified from the urine of mice with the MAC16 tumor. Using a monoclonal antibody to the mice MAC16 protein, a similar protein was also found in the urine of human cachectic cancer patients. The mouse MAC16 protein causes weight loss in rodents, primarily due to a decrease in the lean body mass. The primary bioactivity of this protein is to increase muscle proteolysis and decrease protein synthesis. The MAC16 protein binds tightly to muscle cell membranes. The MAC16 protein also causes some lipolytic activity and does not affect food intake. The protein core of the mouse MAC16 protein has been identified to have at least 18 amino acids and digestion with chondroitinase AC results in a single fragment of 14 kDa. The human protein identified with the monoclonal antibody ("human MAC16") to MAC16 also increases proteolysis in muscle cells. The first 14 amino acids of "human MAC16" are identical to those of mouse MAC16 protein. The human MAC16 has been found only in the urine of cachectic cancer patients, not in patients suffering extreme weight loss from other diseases such as sepsis, burns or major surgery. See P. T. Todorov et al., "Structural Analysis of a Tumor-produced Sulfated Glycoprotein Capable of Initiating Muscle Protein Degradation," The Journal of Biological Chemistry, vol. 272, pp. 12279–88 (1997); P. Cariuk et al., "Induction of Cachexia in Mice by a Product isolated from the urine of cachectic cancer patients," British Journal of Cancer, vol. 76, pp. 606–613 (1997); M. J. Lorite et al., "Induction of muscle protein degradation by a tumour factor," British Journal of Cancer, vol. 76, pp. 1035–1040 (1997); P. Todorov et al., "Characterization of a cancer cachectic factor," Nature, vol. 379, pp. 739–742 (1996); P. T. Todorov et al., "Induction of muscle protein degradation and weight loss by a tumor product," Cancer Research, vol. 56, pp. 1256–1261 (1996); T. M. McDevitt et al., "Purification and Characterization of a Lipid-mobilizing Factor Associated with Cachexia-inducing Tumors in Mice and Humans," Cancer Research, vol. 55, pp. 1458–63 (1995); J. E. Belizario et al., "Bioactivity of skeletal muscle proteolysis-inducing factors in the plasma proteins from cancer patients with weight loss," British Journal of Cancer, vol. 63, pp. 705–710 (1991); S. A. Beck et al., "Lipid mobilising factors specifically associated with cancer cachexia," British Journal of Cancer, vol. 63, pp. 846–850 (1991); P. Groundwater et al., "Alteration of serum and urinary lipolytic activity with weight loss in cachectic cancer patients," British Journal of Cancer, vol. 62, pp. 816–821 (1990); and S. A. Beck et al., "Alterations in serum lipolytic activity of cancer patients with response to therapy," British Journal of Cancer, vol. 62, pp. 822–825 (1990).

At present there is no rational therapy for cachexia, i.e., one based on the etiology of the disease. Since common symptoms of anorexia/cachexia syndrome include loss of appetite, fat deposit, and muscle mass, all existing therapies for cachexia include agents known to increase appetite (e.g., cyproheptadine (PERIACTIN®), facilitate energy storage (e.g., megestrol acetate (MEGACE®)), or increase muscle mass (androgenic agents). While these therapies work for some patients, for many nothing works. Since time is very important for these patients, until a rational therapy can be found, a need exists to predict which patients might respond to which of the various available therapies.

Obesity plays a major role in the etiology of many chronic diseases, including cardiovascular diseases, cancer, and diabetes. Therefore, a national goal has been to reduce the prevalence of obesity in the U.S. population to no more than 20%. Unfortunately, there has been a substantial rise in obesity in U.S. during the last decade.

Obesity is generally classified into two groups based on the site of fat deposition—visceral and nonvisceral, also known as upper-body/android (apple-shaped) and lower-body/gynoid (pear-shaped) obesity, respectively. It is well-established that visceral adipose tissue is associated with greater morbidity and mortality, particularly hypertension, hyperlipidemia, and insulin resistance. Data also show that weight loss by diet, exercise, or pharmacotherapy generates a decrease in visceral adipose tissue and improvements in hypertension, hyperlipidemia, and insulin resistance. See F. X. Pi-Sunyer, "Medical Hazards of Obesity," Annals of Internal Medicine, vol. 119, pp. 655–660 (1993); and G. A. Bray, "Pathophysiology of Obesity," American Journal of Clinical Nutrition, vol. 55, pp. 488S–494S (1992).

A pharmacologic treatment to reduce body fat, particularly visceral fat, would be of great health significance. Currently there is no available pharmacotherapy that will facilitate a decrease in fat deposit. Agents like REDUX™ and Fen/phen have been successful in obesity treatment; however, these agents have been removed from the market due to serious side effects.

We have discovered a proteoglycan ("azaftig") with a molecular weight of approximately 24,000 Dalton that has been isolated and characterized from the urine of cachectic cancer and non-cancer patients. Azaftig has been shown to bind to receptors on fat cell membranes and to cause lipolysis. Azaftig does not bind to muscle cell membranes or cause proteolysis. Azaftig detection in urine will allow early identification of patients in whom weight loss may become a problem. Azaftig may also aid fat loss in humans in whom obesity is a threat to health.

We have isolated a proteoglycan with a molecular weight of approximately 24,000 Dalton from the urine of cachectic cancer and non-cancer patients. We have named this proteoglycan "azaftig." Azaftig has been shown to cause weight loss in mammals. It has also been shown to increase lipolysis and to bind to fat cell membrane preparations. However, unlike the MAC16 glycoprotein, azaftig does not augment proteolysis in muscle tissue or bind to muscle cell membrane preparations.

EXAMPLE 1
Isolation of Azaftig

Urine was collected for 24 hr from a patient with a diagnosis of metastatic adenocarcinoma of unknown primary source, who had experienced a 50 lb weight loss over several months prior to diagnosis. The urine was treated with ammonium sulfate (80% saturation), and incubated overnight at 7° C. The solution was centrifuged at 6,000×g for 1 hr, and the supernatant was removed. The ammonium sulfate precipitate was dissolved in 50 ml of water and centrifuged again. The supernatant was saved, and the pellet was resuspended in 5% sodium dodecyl sulfate ("SDS"). Both the supernatant and the SDS-dissolved precipitate were subsequently separated by SDS-polyacrylamide gel electrophoresis. The supernatant revealed several protein bands, with two predominant bands at 24 kilodaltons and 70 kilodaltons. The proteins with the molecular weight of 24 kilodaltons, or that were later determined to be its multiple (70 kilodaltons), were named azaftigs.

EXAMPLE 2
Characterization of Azaftig

DEAE-Sephacel chromatography

Figure 1:
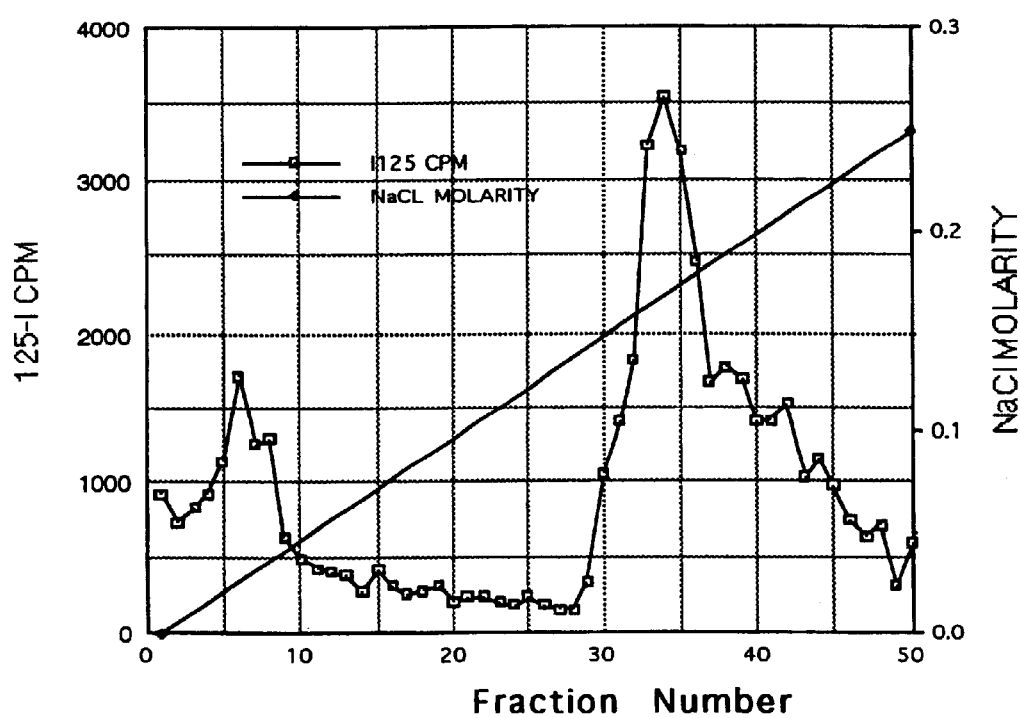
FIG. 1 illustrates the DEAE-Sephacel elution profile of $^{125}$I-azaftig.

Azaftig of 24 kilodaltons was isolated as described above. The purified protein was radiolabeled with $^{125}$I using the chloramine-T method as described by F. C. Greenwood et al., "The preparation of $^{131}$I-labeled growth hormone of high specific activity," Biochemical Journal, vol. 89, pp. 114–123 (1963). The protein was subsequently analyzed for charge using DEAE-Sephacel anion exchange chromatography. $^{125}$I-azaftig was dialyzed overnight at 4° C. against a solution of 8 M urea, 0.1 M Tris, 0.3% Triton X-100, and 0.15 M NaCl (pH 7.0) containing protease inhibitors. The dialyzed sample was applied to a column of DEAE-Sephacel (bed volume 4 ml) that had been equilibrated in the same buffer as the dialyzing solution. The column was washed with 20 ml of the same buffer at a flow rate of 10 ml/h. The column was then eluted with a continuous NaCl gradient (from 0.15 to 1.0 M) in the urea buffer. Fractions of 1.0 ml were collected, and aliquots were counted in a gamma counter to determine $^{125}$I radioactivity. The pattern of eluting at 0.18 M NaCl demonstrated that azaftig is a negatively charged molecule and is likely a proteoglycan, molecules known to have negatively charged sulfate groups (FIG. 1). Consistent with this conclusion, chondroitinase ABC digestion as described by H. Saito et al., "Enzymatic methods of the determination of small quantities of isomeric chondroitin sulfate," J. Biol. Chem., vol. 243, pp. 1536–1542 (1968), of azaftig resulted in a decrease in the azaftig band on SDS-PAGE. Because Chondroitinase ABC is an enzyme that specifically cleaves the chondroitin sulfate or dermatan sulfate groups in proteoglycans, this loss in azaftig indicated that azaftig is a chondroitin sulfate-containing proteoglycan.

Radiolabeled azaftig was separated by SDS-PAGE. Autoradiography demonstrated three to four distinct bands generated by purified azaftig which indicated that azaftig had a tendency to aggregate. To decrease aggregation of the sample, purified azaftig was treated with 1% Triton X-100 and subsequently chromatographed over a Sephadex G-50 column. In addition, experiments were performed in the presence of 4 M guanidine-HCl to minimize aggregation. Both treatments resulted in decreased aggregation as seen by a single band by SDS-Page, demonstrating that azaftig forms aggregates in vitro. Subsequent studies with anti-azaftig antibody have also demonstrated a similar aggregation pattern, as described in Example 3 below.

Enzymatic digestion $^{125}$I-azaftig was digested in separate experiments by using 50 each units of neuraminidase, chondroitinase ABC, or chondroitinase AC. Each digestion product was analyzed by SDS-PAGE electrophoresis. Neuraminidase did not degrade the proteoglycan, while chondroitinases ABC and AC caused partial digestion. Chondroitinase AC produced fragments with molecular weights below 10 kDa. These data confirm that azaftig is a proteoglycan, because both chondroitinase ABC and AC specifically cleave the chondroitin sulfate or dermatan sulfate found in proteoglycans.

EXAMPLE 3
Development of Western Blot Assay

Production of antibody to azaftig

Five μg of purified azaftig electroeluted from SDS-PAGE gels was injected into New Zealand White rabbits using complete Freund's adjuvant (Difco Laboratories, Detroit, Mich.). Subsequent immunizations were performed using the same amount of azaftig in incomplete Freund's adjuvant every two weeks for a total of four injections. After four immunizations, the rabbits were bled, and the antisera, with its polyclonal antibodies, were tested against the purified azaftig and the original urine samples from the patient. As demonstrated by Western Blot, the antiserum bound azaftig at a 1:1,000 dilution. This antiserum was then used for the detection of azaftig in HIV/AIDS patients with weight loss.

Additional polyclonal and monoclonal antibodies to the azaftig molecule can also be made by a person with ordinary skill in the art using techniques well known in the field.

Western blot methods

Proteins from a patient's unconcentrated urine were separated by 14% SDS-PAGE, and transferred to nitrocellulose by the method of H. Towbin et al., "Electrophoretic transfer of proteins from polyacrylamide gels to nitrocellulose sheets: Procedure and some applications," Proc. Natl. Acad. Sci. U.S.A., vol 76, pp. 4350–54 (1979). The transferred proteins were then probed with the anti-azaftig antibody. After development with an alkaline phosphatase-conjugated goat anti-rabbit immunoglobulin, a semiquantitative assessment was made of the intensity of the bands present on the blot.

EXAMPLE 4
Screening for Azaftig in Non-cancer, HIV Patients

Forty-two HIV-positive patients were chosen at random to provide urine samples and to complete a questionnaire concerning weight loss, opportunistic infections, and other parameters of HIV activity. All 42 were screened by the Western Blot method discussed above. Of the 42 patients, 17 were found not to have azaftig. Ten had large amounts of azaftig in the urine, while the remaining 15 had modest amounts of azaftig. Twenty-four patients (13 with azaftig and 11 without azaftig) completed questionnaires that solicited weight information. Table 1 presents the data concerning the presence of azaftig and weight loss in these patients.

TABLE 1

| | Azaftig in Urine | | |
|---|---|---|---|
| | Present | Absent | Total |
| Weight Loss | 9 | 4 | 13 |
| No Weight Loss | 4 | 7 | 11 |
| Total | 13 | 11 | 24 |

Thus in the 24 patients, 13 patients had experienced weight loss, and 9 of these 13 (69.2%) had azaftig in their urine. Of the 11 patients that had not experienced any weight loss, only 4 (36.4%) had azaftig in their urine. Therefore, in this sample population, patients with azaftig were almost twice as likely to experience weight loss as those without azaftig. Likewise, patients with weight loss were almost twice as likely to express azaftig as those without weight loss. However, the sample size was not sufficiently large to show statistical significance ($p=0.10$).

One explanation for the small number of patients who exhibited measurable quantities of azaftig but did not experience weight loss may be differences in the structures of azaftig produced by different individuals.

EXAMPLE 5
Concentrations of Azaftig in Cancer Patients

Twenty-three hospitalized cancer patients, seven non-cancer patients, and ten healthy adults were randomly selected. The non-cancer patients had been diagnosed with diabetes, emphysema, anemia, hypertension and coronary heart failure. The participants were asked to complete questionnaires detailing their eating habits and any pattern of weight loss or gain. Of the 23 cancer patients, seven reported weight loss, three no weight loss, and thirteen did not respond to the questionnaire. Of the seven non-cancer patients, only two patients with coronary heart failure reported weight loss. The extent of weight loss was not determined by the questionnaire. The total urine volume produced by each patient over 24 hr was collected, and a portion was analyzed by SDS-PAGE. The intensity of the azaftig band in each sample was quantified using NIH Image software (v. 1.59). Known concentrations of purified bovine serum albumin (BSA) were analyzed in the same manner to generate a standard curve. The concentration of azaftig in patient samples was determined by comparing the integrated densities for patient samples with band densities of known concentrations of BSA. The mean concentration of azaftig in the patients with cancer was $8.37 \pm 12.51$ mg/L, with a range of 0.00 to 39.25 mg/L. These data demonstrated a great deal of variability in the levels of azaftig in cancer patients. The non-cancer patients and healthy adults all had azaftig levels of 0.00 mg/L. It was interesting that the only non-cancer patients reporting weight loss were patients diagnosed with cardiac failure, a disease associated with cachexia. Without wishing to be bound by this theory, it is possible that these two patients were showing incipient signs of cachexia, but that azaftig had not yet reached measurable levels.

EXAMPLE 6
Azaftig Causes Weight Loss in Mammals

Weight Loss in Rats

Figure 2:
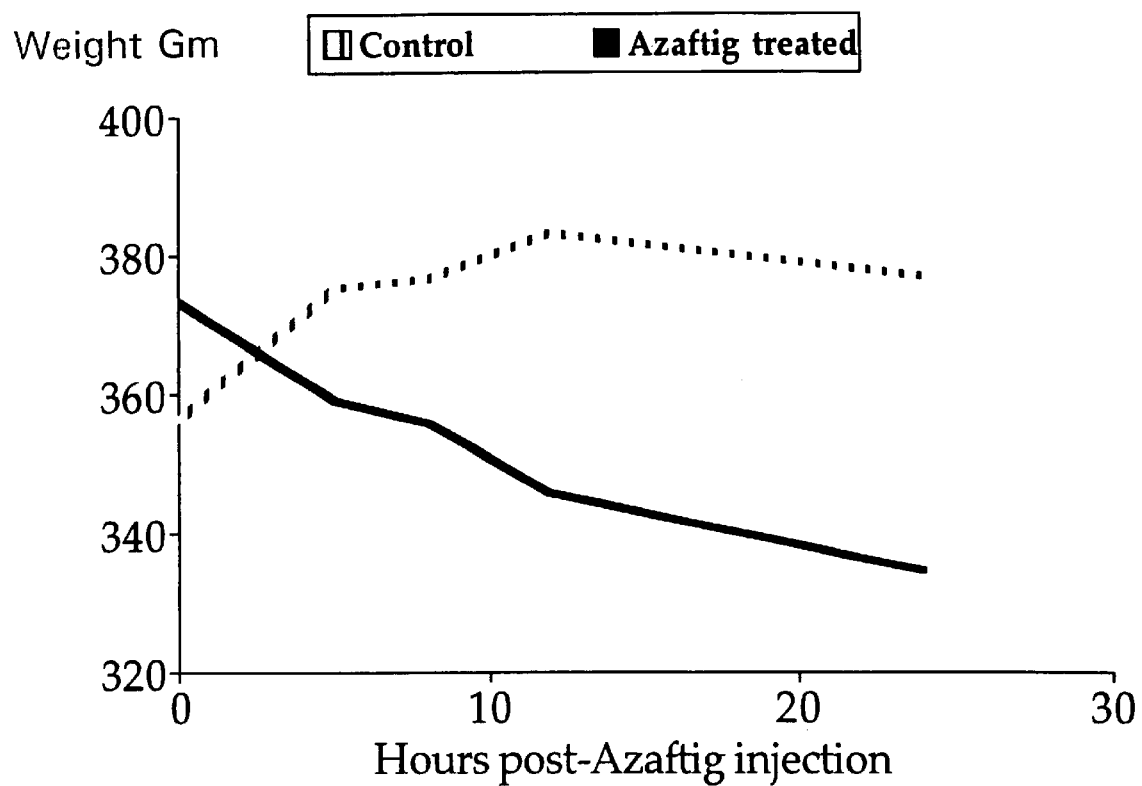
FIG. 2 illustrates the decrease in the body weight of a rat due to azaftig injections.

Two Sprague-Dawley rats were cannulated in the carotid artery and their weights allowed to stabilize after the operation. At the end of five days, one rat was given three doses (at 5 hr intervals) of purified azaftig at 1 μg/gram body weight, administered in phosphate buffered saline. The azaftig was isolated from a human cancer patient. The other rat received only buffered saline. As seen in FIG. 2, the control rat gained weight over 24 hr, while the azaftig-treated rat lost 10% of its body weight over the same period. This preliminary experiment demonstrated that the azaftig caused weight loss in another mammalian species.

Weight Loss in Mice

Figure 3:
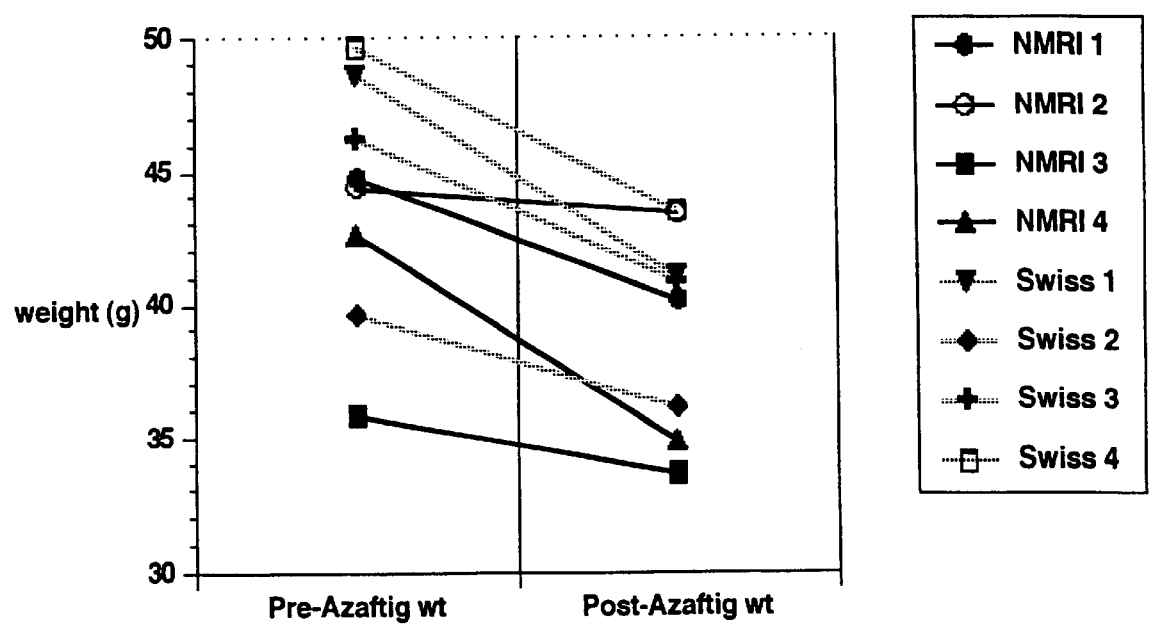
FIG. 3 illustrates the decrease in the body weight of mice due to azaftig injections.

Similar studies were performed on four inbred NMRI mice (Charles River, Willinington, Mass.) and four outbred NIH Swiss mice (Hilltop Laboratories, Scottsdale, Pa.). Initially, the mice were injected intraperitoneally with an elution buffer of 0.1% SDS in 50 mM ammonium acetate for five days until their weights became stable. After weight stabilization, the mice were injected daily with 0.1 mg/kg of gel-purified azaftig for five days. Daily body weight and food intake were recorded. As shown in FIG. 3, the eight mice lost weight at an average of 12.0% (±7%) of maximal measured body weight. This reduction is significant in a paired t-test (p=0.001) using the pre-azaftig weight of each animal as a control for post-treatment weight.

Figure 4:
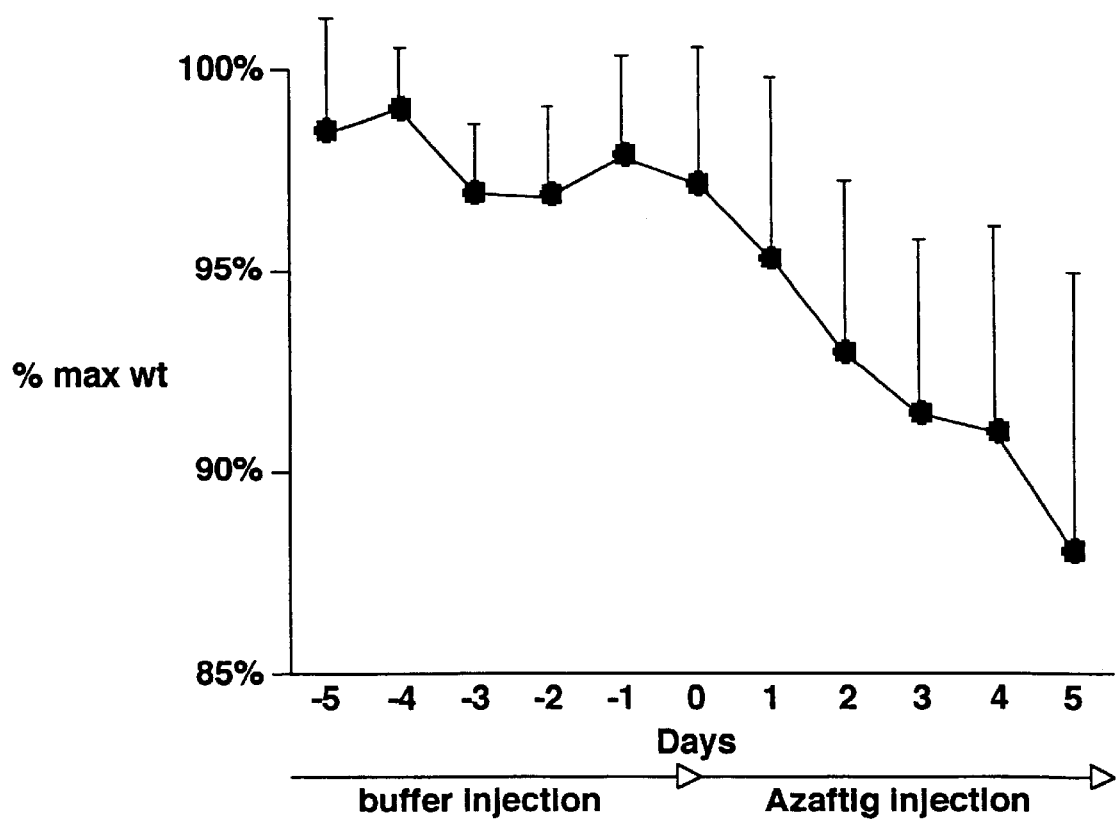
FIG. 4 illustrates the time course of the weight loss of mice seen in FIG. 3.

In FIG. 4, the data are plotted to display the time course of weight loss with the administration of azaftig Because the mice had different initial weights, the data are expressed as percentages of the maximum weight seen with each animal (mean±SD) during the experiment. These data demonstrate that azaftig administration causes substantial and sustained weight loss.

Figure 5:
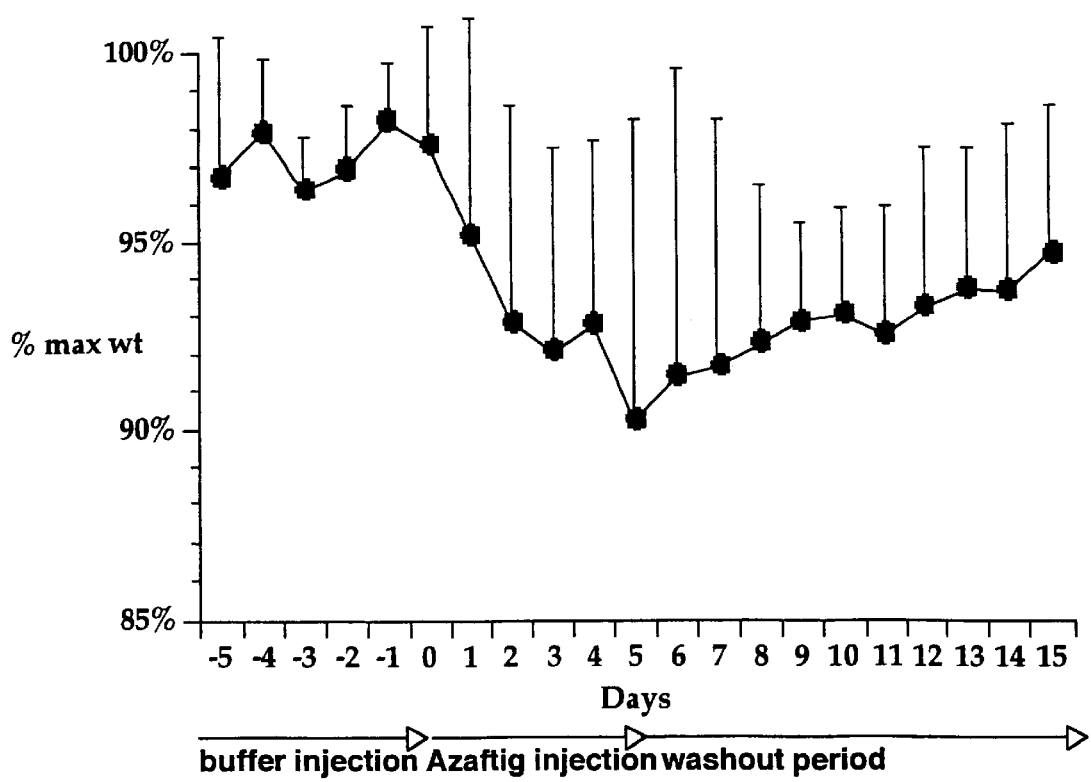
FIG. 5 illustrates the time course of weight gain in mice after ceasing azaftig injections.

To determine whether the azaftig effect was reversible, four mice of the original eight were allowed to recover after discontinuing the injection of azaftig. As shown in FIG. 5, these animals slowly regained lost weight, but did not return to baseline. An autopsy was performed on these four mice. The mice were found to have little to no intra-abdominal fat. This suggested that although the weight was regained, the weight increases were not due to an increase in fat mass.

EXAMPLE 7
Effect of Azaftig on Intraperitoneal Fat

Figure 6:
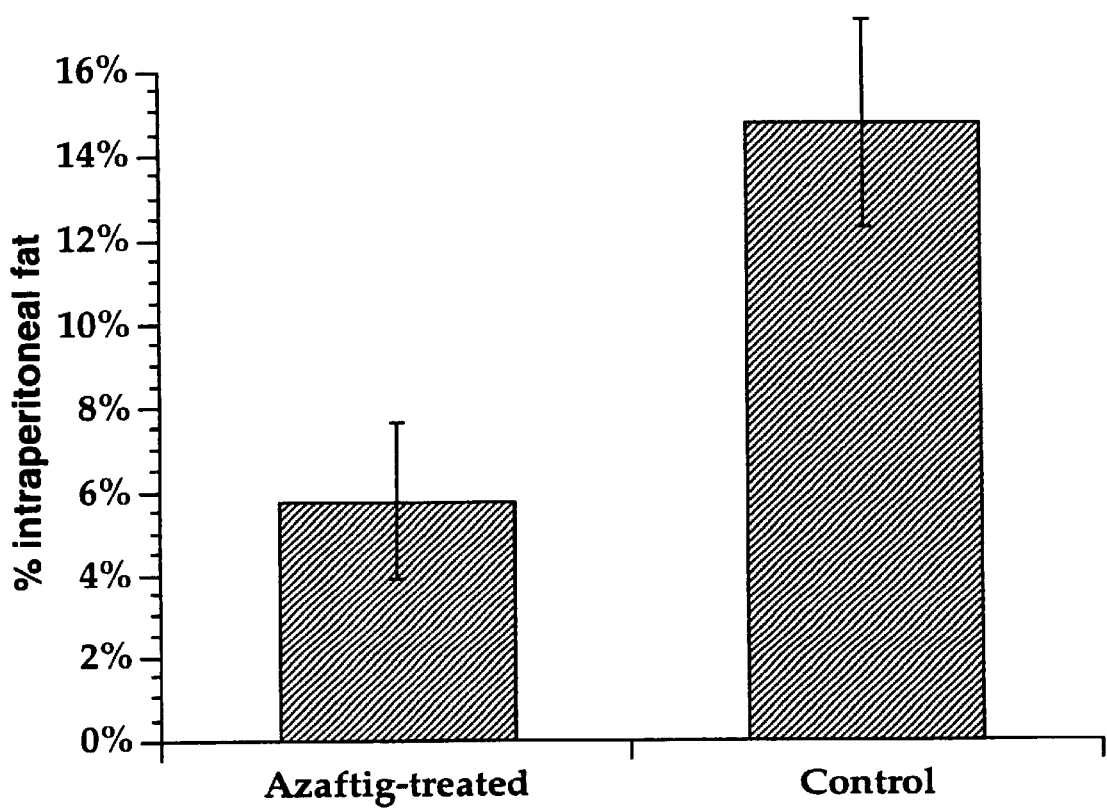
FIG. 6 illustrates the decrease in percent intraperitoneal fat in azaftig-treated mice as measure one week after the last azaftig injection.

To further confirm the above observation that weight gain was not due to fat, five mice were given 0.1 mg/kg azaftig intraperitoneally daily for five days. One week after the last azaftig administration, the mice were weighed and sacrificed. Intraperitoneal fat was surgically removed and weighed. The percent intraperitoneal fat of total body weight was calculated and the results shown in FIG. 6. Animals that had not received an injection served as controls. Azaftig-treated animals showed a significant reduction (60%) in the percentage of intraperitoneal fat as compared with controls. The mean percentage intraperitoneal fat (±standard deviation) for azaftig-treated animals was 5.75%±1.83; for control animals, 14.7%±2.44 (p=0.002).

EXAMPLE 8
Effect of Azaftig on Food Intake

Figure 7:
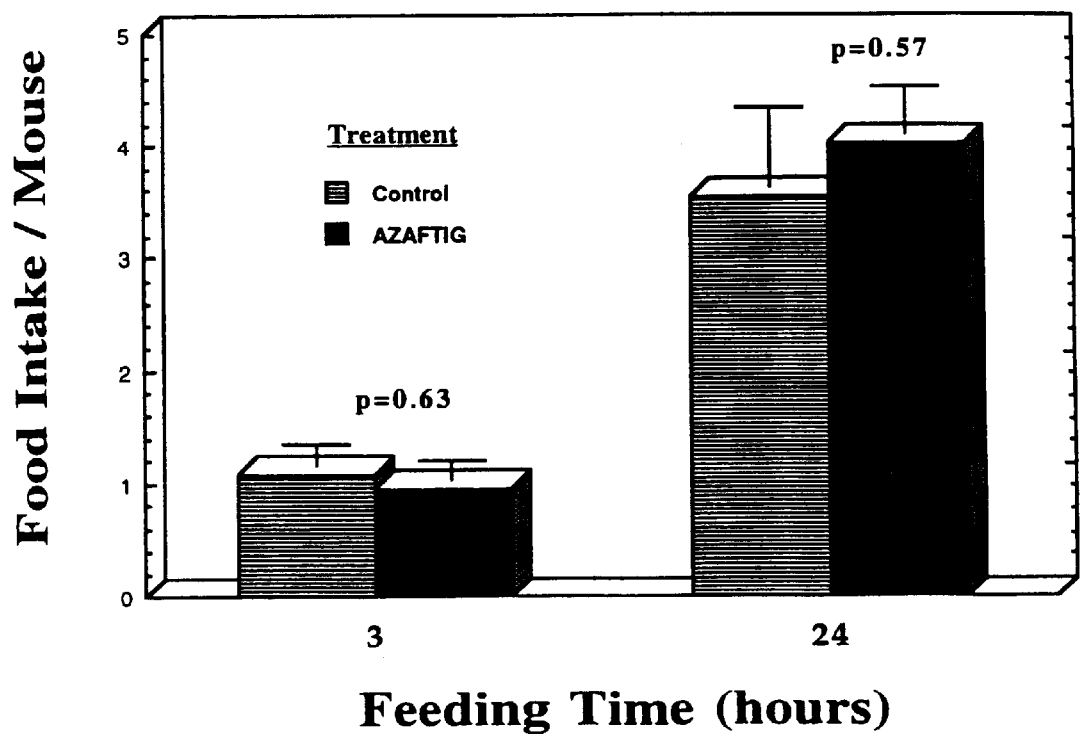
FIG. 7 illustrates the food intake at 3 hr and 24 hr for control and azaftig-treated mice.

To ascertain the effect of azaftig on appetite, experiments were performed on fasted mice. Eighteen female NIH Swiss mice were divided into two groups, a control and treatment group of nine mice each. The mice were kept from food, but not water, for 21 hr and then fed for 3 hr on five consecutive days. On day six, 30 min before the scheduled feeding time, the mice were treated intraperitoneally either with vehicle (0.1 ml/mouse) or with azaftig (0.1 mg/kg in 0.1 ml vehicle). Thirty minutes later, food was presented. At 3 hr and 24 hr food intake for each mice was measured. The data presented in FIG. 7 show that azaftig did not significantly affect food intake at either 3 hr or 24 hr.

EXAMPLE 9
Demonstration of Azaftig Receptors on Fat Cells

Preparation and purification of $^{125}$I-azaftig

Azaftig was labeled using a lactoperoxidase $^{125}$I-labeling kit purchased from ICN Radiochemicals. Briefly, 1.5 mCi neutralized carrier-free $^{125}$I (10 µl) was added to a tube containing 30 µg azaftig (100 µl) and mixed thoroughly. Ten µl of lactoperoxidase solution (1 µg/µl) in water was added to the above mixture. The reaction was initiated by adding 5 µl of 3% freshly prepared $H_2O_2$. The addition of $H_2O_2$ was repeated three times at 10 min intervals until a total of 40 µl $H_2O_2$ was added. Ten min after the last addition, the reaction was terminated by dilution with 500 µl of 50 mM potassium phosphate buffer, pH 7.5. The total mixture was loaded on a Sephadex G-25 column with a bed volume of 9 ml. The column was eluted with the above phosphate buffer, and 14 one-ml fractions were collected. The peak of radioactivity appeared between fraction 4 and 7, and was pooled. This pooled sample was mixed with 1/10th volume of 5% bovine serum albumin, and stored at −20° C. in 1.2 ml aliquots.

Figure 8:
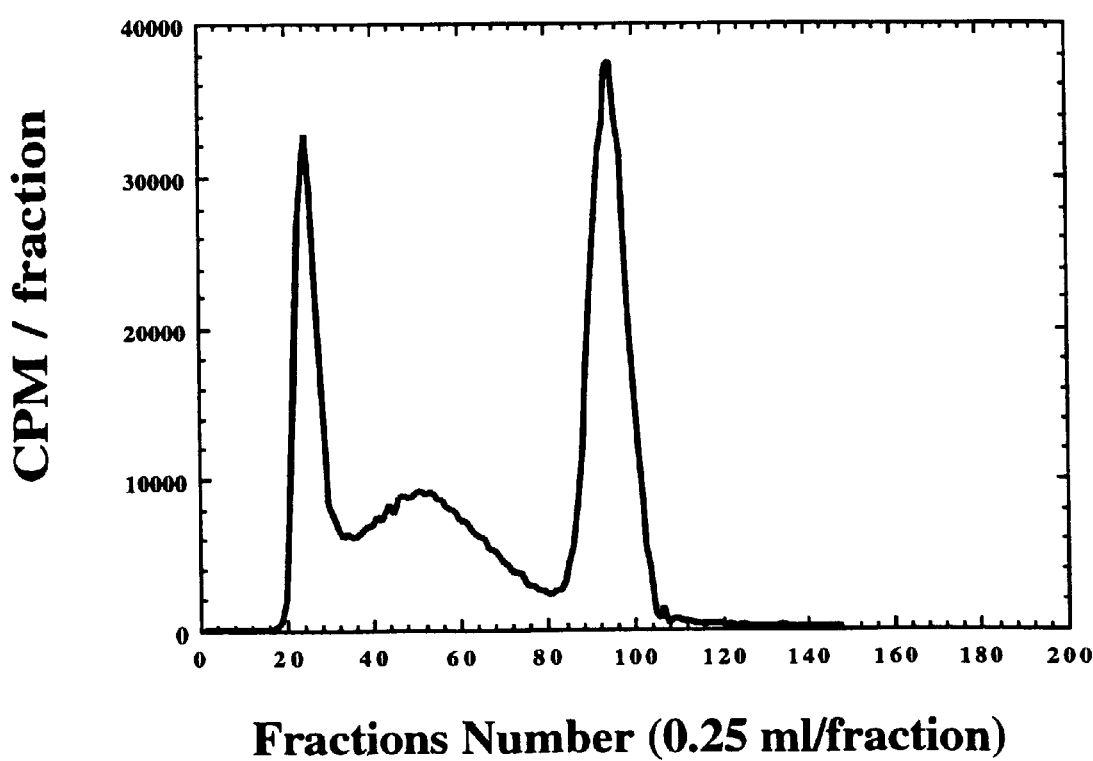
FIG. 8 illustrates the Sephadex G-25 elution profile of $^{125}$I-azaftig.

The $^{125}$I-azaftig was further purified before receptor binding by loading a 1.2 ml sample with 164,400 CPM on a Sephadex G-25 column (58×0.75 cm, bed volume of 25.6 ml). The column was eluted with 50 mM Tris-HCl (pH 7.5) containing 0.15 M NaCl, and 148 fractions (0.25 ml/fraction) were collected and counted for radioactivity. The data presented in FIG. 8 show three peaks of radioactivity with Peak 3 being the free $^{125}$I. Following SDS PAGE, Peak 1 migrated with known azaftig whereas Peak 2 appeared to be a degradation product. Only the Peak 1 product, at fractions 18 to 36, was used in subsequent receptor binding assays.

Preparation of fat cell membranes

Adult female NIH Swiss mice (30–35 grams) were killed by cervical dislocation, and visceral fat was collected from the abdominal cavity. The fat (200–300 mg) was suspended in 10 ml of ice-cold 50 mM Tris-HCl, pH 7.4, and minced with scissors until a good suspension of cells was achieved. The suspension was kept cold while it was homogenized with a Virtis Polytron for 20 sec at a setting of 2.5. The homogenate was centrifuged at 3,000×g for 10 min at 4° C. The supernatant was recentrifuged at 49,000×g for 15 min at 4° C., and the pellet collected. The pellet was then resuspended in the homogenizing buffer at 20 mg original tissue/ml, and mixed with the Polytron for 5 seconds. This sample was then used for receptor binding.

Binding Assay

For the binding assay, 300 µl of membrane preparation, 10 µl of buffer (50 mM Tris-HCl, pH 7.4) (with or without non-radioactive azaftig), and 10 µl of $^{125}$I-azaftig (300–500 pmol) was incubated over ice for 15 min. The reaction was stopped by addition of 5 ml of ice-cold buffer. The membrane-bound $^{125}$I-azaftig was immediately collected by suction through a glass microfibre filter with a one-micron pore size (Whatman Co.), followed by two 5-ml washings with buffer. The whole process of filtration and washing took about 15 sec. The filters were transferred to a scintillation vial, and radioactivity was counted in a gamma-counter. Specific $^{125}$I-azaftig binding was calculated by subtracting the non-specifically bound radioactivity from the total bound radioactivity not displaced by 1.0 µM azaftig.

Optimal Conditions for $^{125}$I-azaftig binding

Figure 9A:
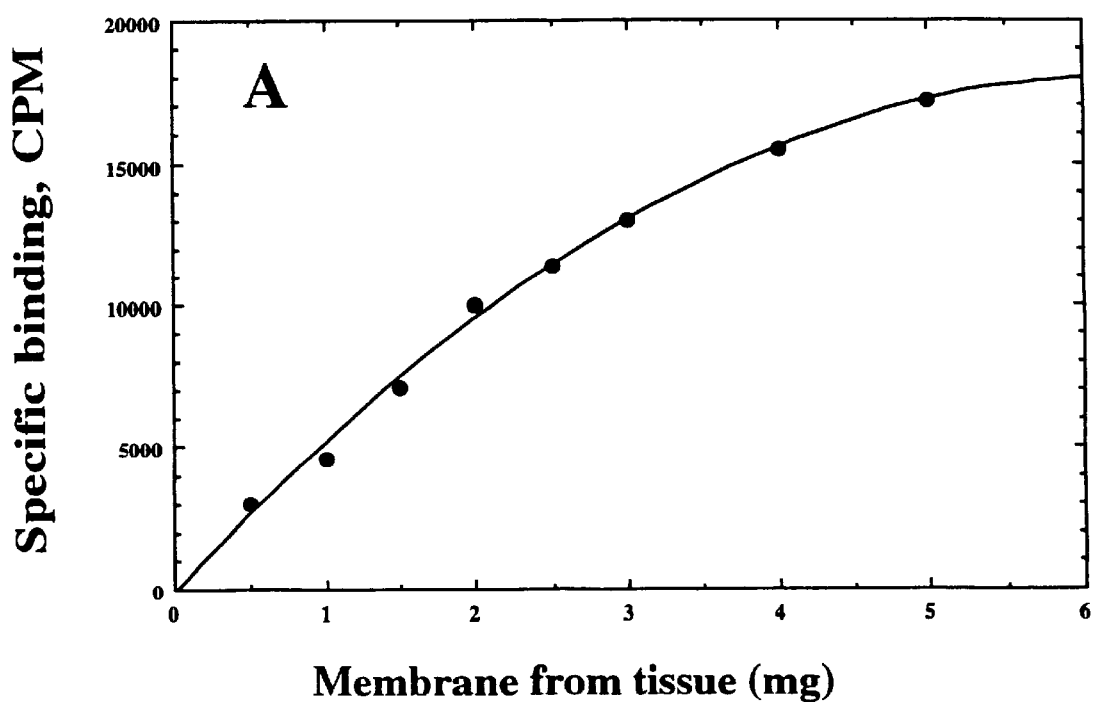
FIG. 9A illustrates the specific binding of $^{125}$I-azaftig to fat cell membrane preparations.
Figure 9B:
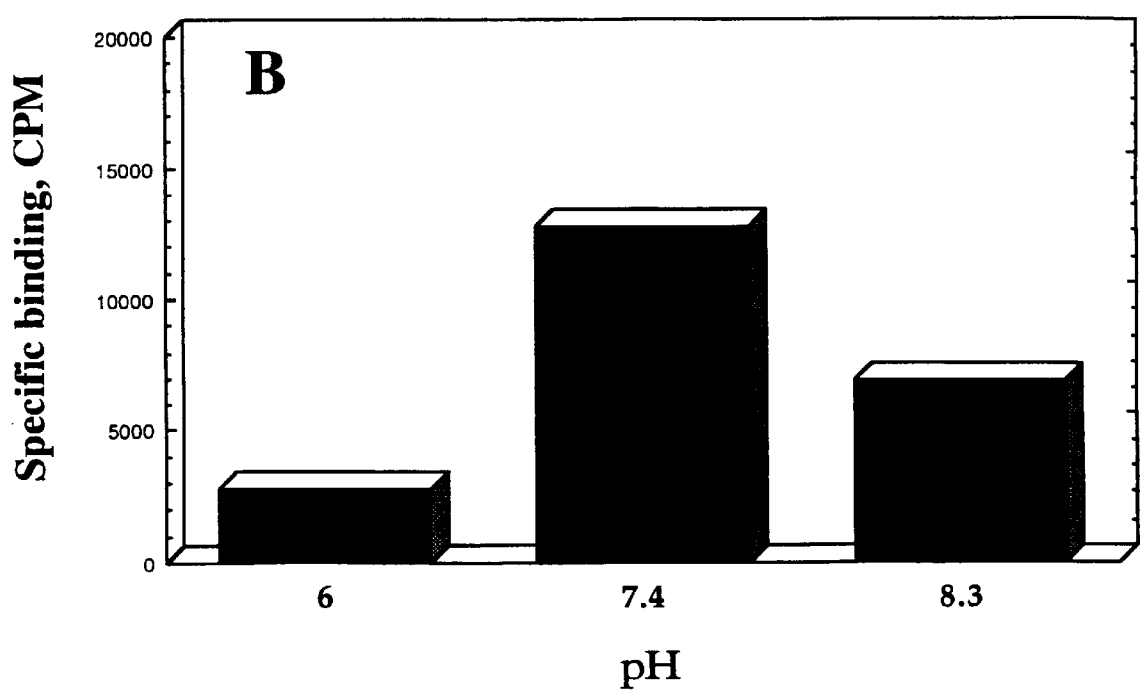
FIG. 9B illustrates the effect of pH on the specific binding of $^{125}$I-azaftig to fat cell membrane preparations.
Figure 9C:
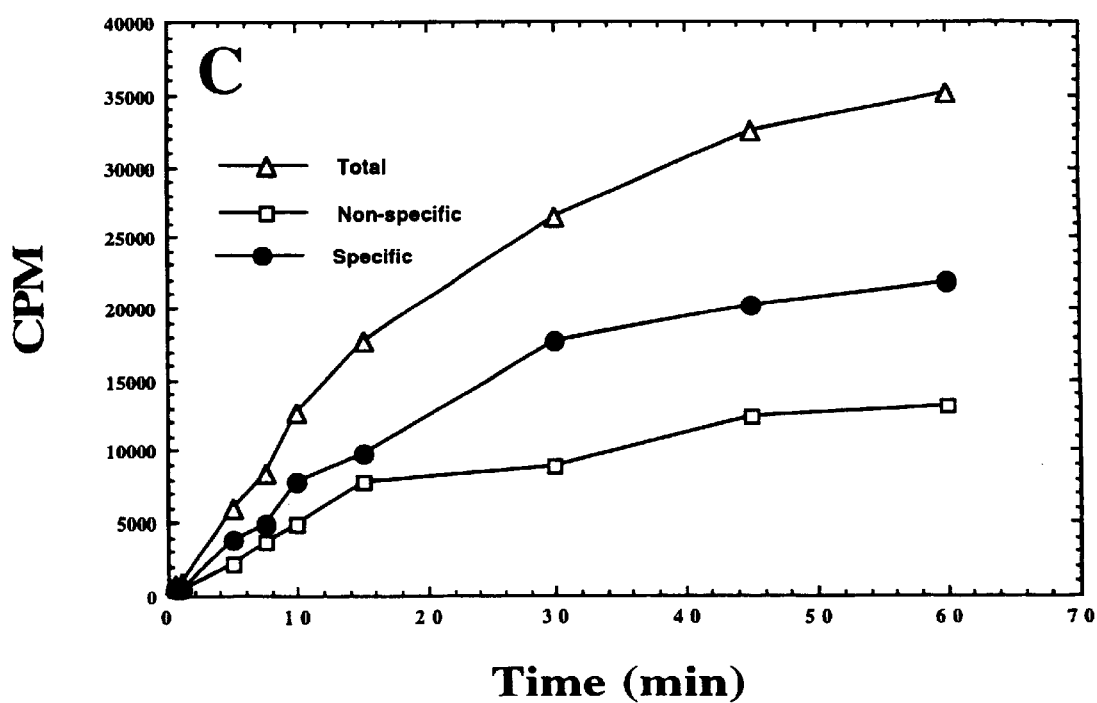
FIG. 9C illustrates the time dependence of specific binding of $^{125}$I-azaftig to fat cell membrane preparations.

Specific binding of $^{125}$I-azaftig to fat cell membrane preparations was dependent upon membrane protein concentration, pH, and the duration of incubation (FIGS. 9A, 9B, and 9C). At a temperature of 0 to 4° C. and pH 7.4, the specific binding of $^{125}$I-azaftig was proportional to the membrane protein concentration, which varied from 0.5 to 5.0 mg tissue per tube (FIG. 9A). The specific binding was the highest at neutral pH (FIG. 9B). At 4° C. and pH 7.4, the specific binding of $^{125}$I-azaftig increased linearly with time, reaching a maximum at 15 min (FIG. 9C).

Saturation of $^{125}$I-azaftig binding

Figure 10A:
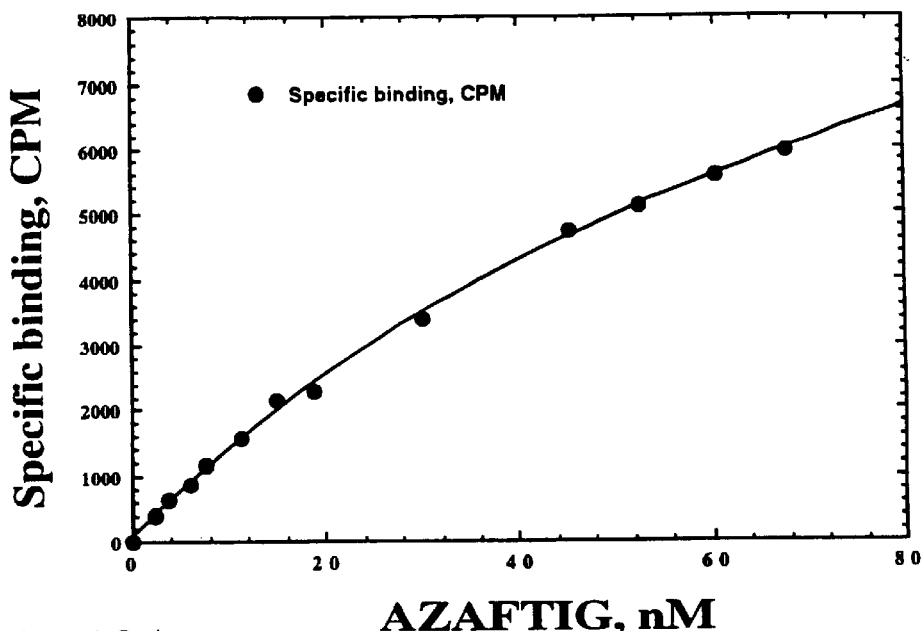
FIG. 10A illustrates the effect of concentration of $^{125}$I-azaftig on specific binding to fat cell membrane preparations.
Figure 10B:
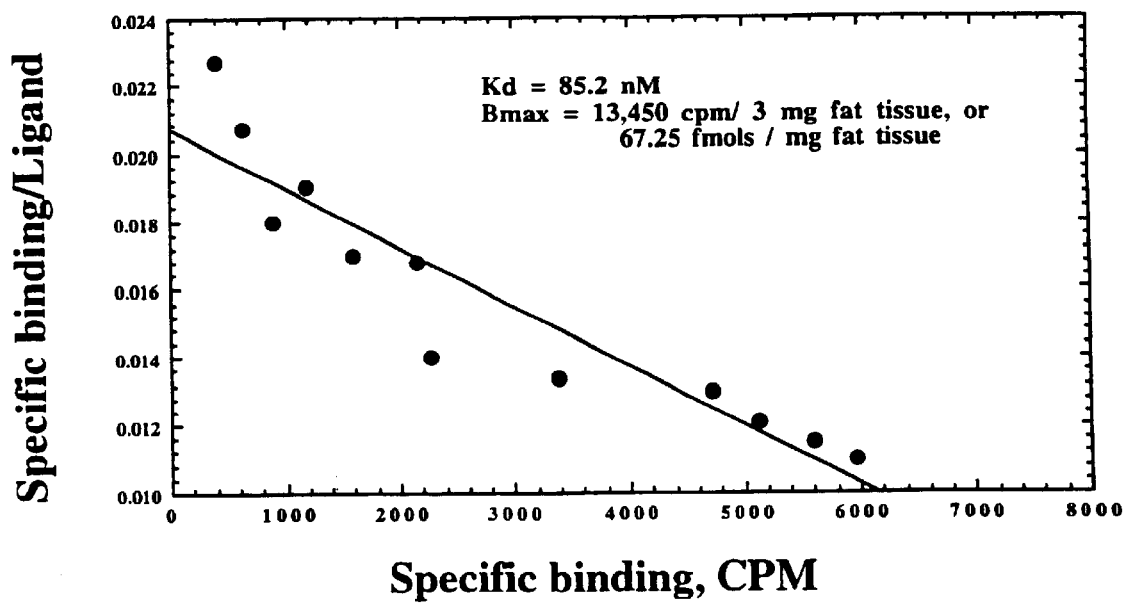
FIG. 10B illustrates the Scatchard analysis of the binding data from FIG. 10A.

Addition of increasing amounts of $^{125}$I-azaftig to a fixed amount of receptor preparation resulted in saturation of specific binding (FIG. 10A). The Scatchard analysis of these binding data (FIG. 10B) indicated the presence of a single population of binding sites with an apparent dissociation constant (KD) value of 85.2 nM and maximal binding capacity ($B_{max}$) of 67.25 fmols/mg fat tissue.

EXAMPLE 10
Azaftig Does Not Promote Protein Degradation in Muscles, nor Bind to Muscle Cells Muscle tissue incubated in vitro undergoes proteolysis, resulting in loss of muscle tissue and release of amino acids.

This proteolysis can be augmented by the addition of the glycoprotein MAC16, which also increases lipolysis. Using methods as described by P. Todorov et al., "Structural analysis of a tumor-produced sulfated glycoprotein capable of initiating muscle protein degradation," J. Biol. Chem., vol. 272, pp. 12279–12288 (1997), azaftig, by contrast, did not augment muscle degradation.

Figure 11:
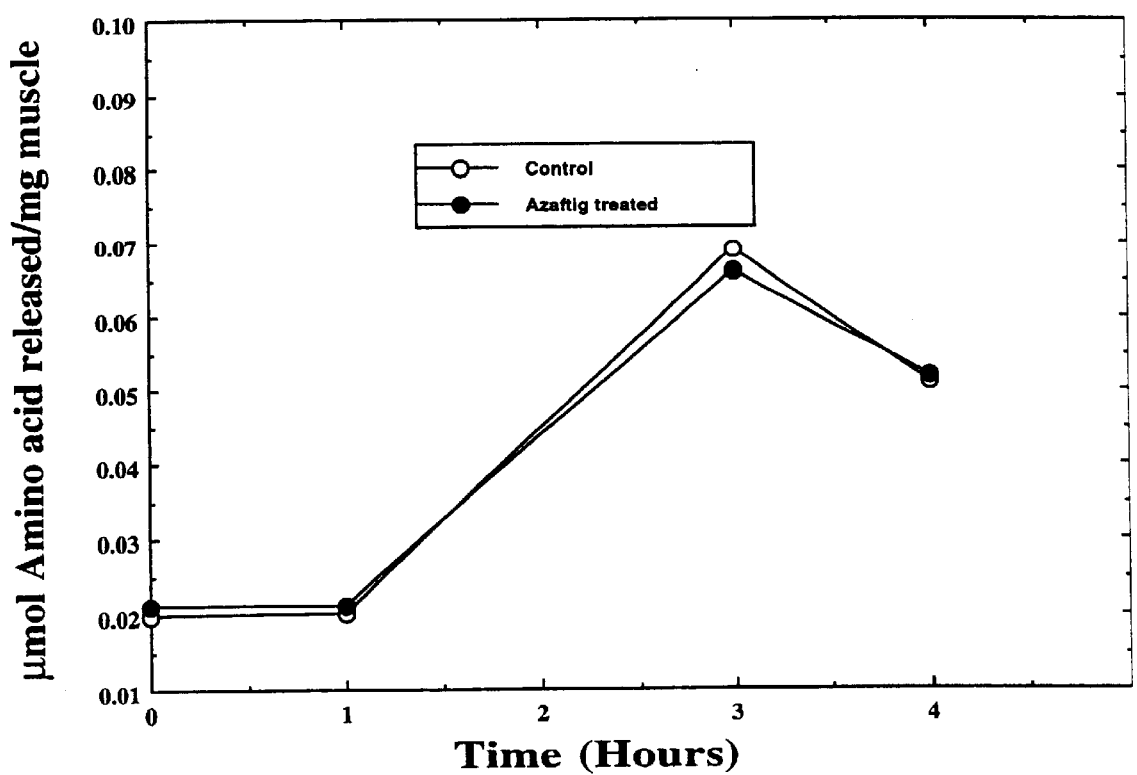
FIG. 11 illustrates the effect of azaftig on in vitro muscle cell proteolysis.

The diaphragm muscle was dissected from two mice, cleaned of extraneous tissue, and weighed, 67.2 and 66.3 mg. Each diaphragm muscle was transferred into a small vial containing 1 ml Krebs-Ringer bicarbonate buffer, pH 7.4, with 0.1% glucose. The vial was gassed with air containing 5% carbon dioxide and allowed to incubate for 30 min at 37° C. The muscle tissue was then removed, blotted, and transferred to a clean vial containing either 1 ml Krebs-Ringer buffer (control) or 1 ml of Krebs-Ringer buffer containing 150 µg of azaftig (experimental). The vials were then gassed as above and allowed to incubate for 2 hr at 37° C. At the end of incubation, the muscle was removed, washed three times with phosphate-buffered saline, and transferred to a clean vial containing 3 ml of the Krebs-Ringer buffer. A 0.5 ml aliquot of the solution was removed immediately for the zero time determination of amino acids released by proteolysis. The muscle was then incubated at 37° C. and similar aliquots drawn at 1 hr, 3 hr, and 4 hr. The amino acids were assayed by the ninhydrin method as described by S. Moore, "Amino acid analysis: Aqueous dimethyl sulfoxide as solvent for the ninhydrin reaction," J. Biol. Chem., vol. 243, pp. 6281–6283 (1968). As shown in FIG. 11, the azaftig-treated muscle released amino acids at the same rate as the control. Azaftig did not augment the normal proteolytic rate.

Radiolabeled $^{125}$I-azaftig was incubated with membrane preparations from a variety of tissues, including heart, muscle, adrenal, kidney, liver, and fat cells. Only the fat cells showed binding indicating a high affinity receptor. Muscle cells did not bind the $^{125}$I-azaftig and were used as controls in later receptor assays.

EXAMPLE 11

Half-life of Azaftig

NIH Swiss mice were treated twice daily with azaftig (0.5 mg/kg, intraperitoneal injection) on five consecutive days. Food intake and changes in body weight were measured daily. The onset of weight loss after azaftig administration was delayed by 1–2 days. Weight loss, however, continued for several days after termination of azaftig treatment. The loss of the visceral fat deposit in mice was clearly visible several days after termination of treatment. To understand the mechanism underlying the azaftig-mediated weight loss and decrease of the fat deposit, the blood half-life of $^{125}$I-azaftig in Swiss Webster mice was measured.

Figure 12:
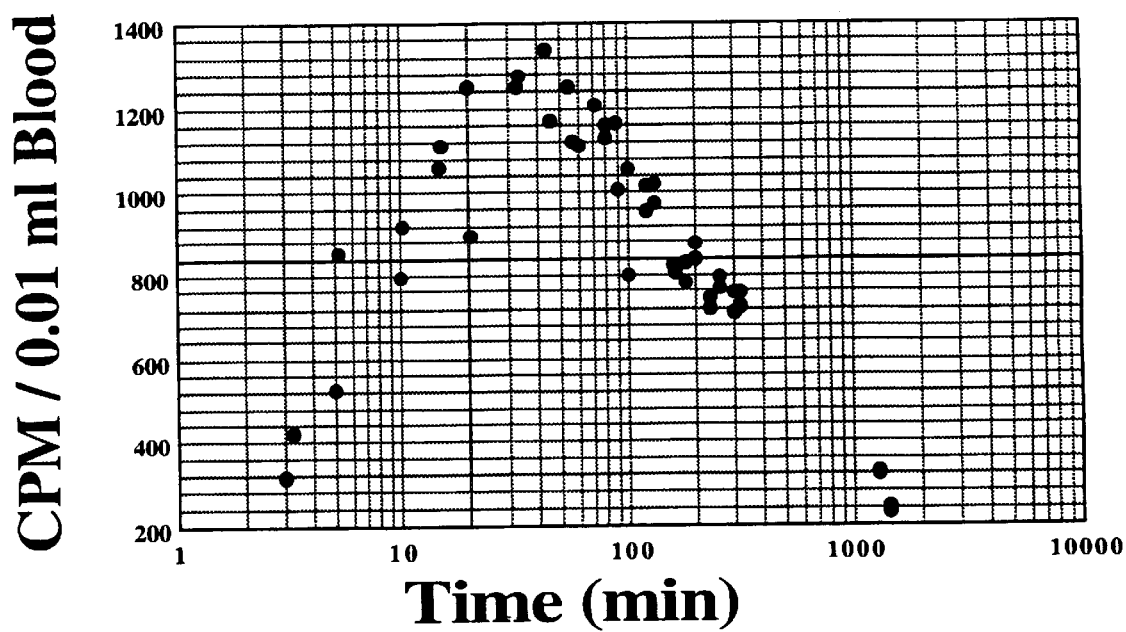
FIG. 12 illustrates the rate of blood clearance in mice of $^{125}$I-azaftig.

Five adult female NIH Swiss mice from Hilltop Farm were injected intraperitoneally with 0.1 ml $^{125}$I-azaftig ($5\times10^6$ CPM, 5 µg azaftig). At various times 10 µl blood was collected from the tail and radioactivity of the blood sample was determined in a gamma-counter. The data presented in FIG. 12 show a radioactivity profile in a typical mouse. Radioactivity in the blood reached a maximum of about 1300 CPM/10 µl in about 20 min and remained elevated for about 30 min. Then the level of radioactivity in the blood declined slowly with a half-life of approximately 4 to 5 hr, indicating a slow clearance rate for azaftig. This slow clearance is indicative of azaftig resistance to metabolic degradation and makes azaftig a potent cachectic agent.

EXAMPLE 12

Sequencing of Azaftig

The purified azaftig was used in an initial attempt to sequence the protein core of the proteoglycan. Unfortunately, the amino terminus was found to be blocked. By contrast, the amino terminus of the MAC-16 protein is not similarly blocked. See Cariuk et al., 1997.

Once 10 µg of azaftig is purified as described below in Example 13, the azaftig protein core will be sequenced by first cleaving the molecule and then sequencing the unblocked segments by methods known in the field.

EXAMPLE 13

A Three Step Purification for Azaftig

A three-step method was developed to further purify the azaftig.

Step 1: DEAE-Sephacel chromatography

Figure 13:
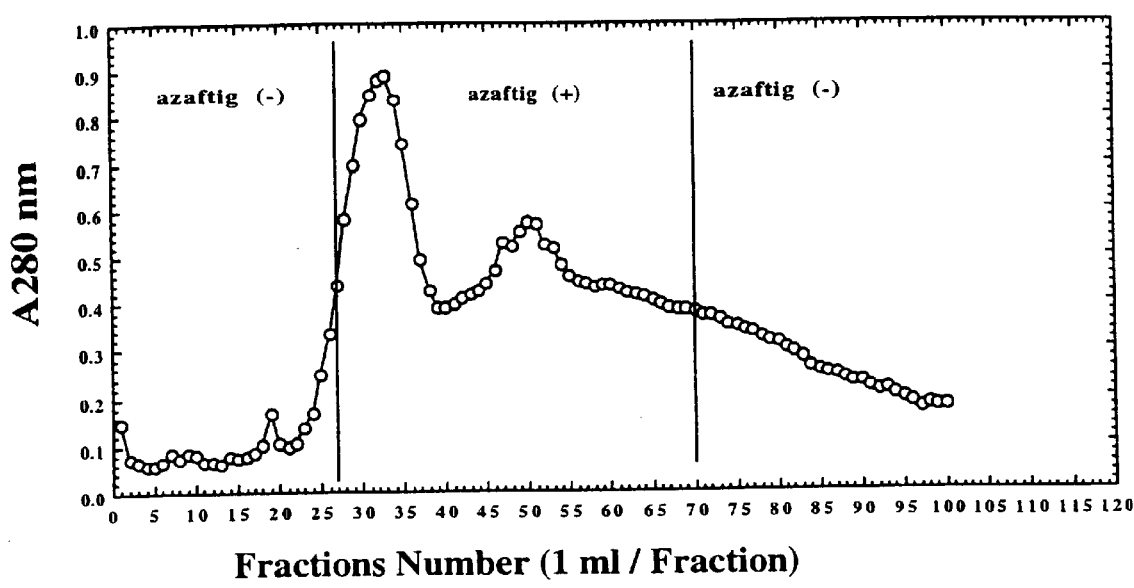
FIG. 13 illustrates the DEAE-Sephacel elution profile of azaftig.

Two hundred milliliters of urine from a cachectic cancer patient was passed through a DEAE-Sephacel column (4.0 ml bed volume) at a flow rate of 10 ml/hr. The column was washed with 20 ml of a 0.05 M sodium acetate buffer, pH 6.0, containing 0.5% Triton X-100 and 8 M urea, and then eluted with a continuous NaCl gradient from 0 to 0.3 M in the same buffer. Fractions of 1 ml were collected, and aliquots were tested for protein by measuring absorbance at 280 nm. Fractions with protein were subjected to SDS-Page, transferred to nitrocellulose membranes, and probed with the antibody to azaftig. As shown in FIG. 13, fractions 27–70 showed positive immunoreactivity. The highest immunoreactivity was found between fractions 33–41. Fractions 33, 37, and 41 were pooled for further purification.

Step 2: Q-Sepharose chromatography

Figure 14:
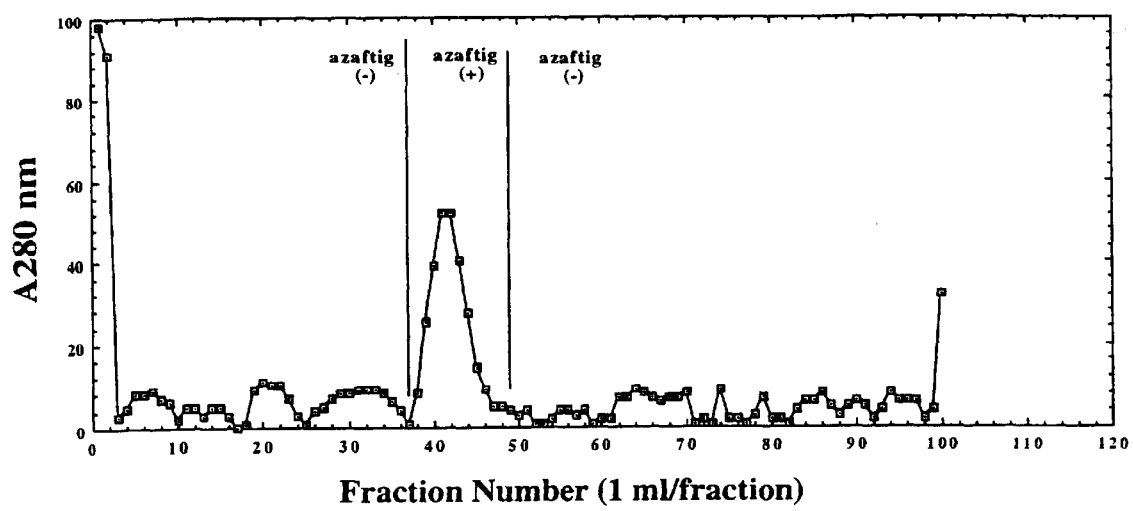
FIG. 14 illustrates the Q-Sepharose elution profile of azaftig.

The pooled fractions from Step 1 were dialyzed against 0.01 M Tris-HCl, pH 8.0 for 24 h at 4° C., and then applied to a Q-Sepharose column (8.0 ml bed volume). The column was washed with 20 ml of 0.01 M Tris-HCl buffer, pH 8.0, and then eluted with a 0 to 0.3 M NaCl gradient in the same buffer at a flow rate of 10 ml/h. Fractions of 1 ml were collected and tested for protein by measuring absorbance at 280 nm. Fractions with protein were subjected to Western blot analysis using the azaftig antibody as described above. As shown in FIG. 14, fractions 38–48 showed positive immunoreactivity, with the highest activity in fractions 41 and 42. Fractions 41 and 42 were pooled for further purification.

Step 3: High Pressure Liquid Chromatography (HPLC)

The pooled sample of fractions 41 and 42 from Step 2 was injected into a HPLC column (Novo-pack $C^{18}$ 60A 4 µm, 3.9×300 mm, 40° C.). The column was eluted at a flow rate of 0.5 ml/min using a linear gradient from 0.1% to 35% of acetonitrile in 0.1% trifluoroacetic acid and 0.05% triethylamine. Each fraction was recorded for absorbance at 214nm and tested for immunoreactivity against azaftig antibody. The azaftig eluted from the column in about 6 min.

EXAMPLE 14

Detection of Azaftig as a Diagnostic Tool

A detection system for azaftig will be developed to identify patients at risk of experiencing cachexia from cancer, HIV infection, or other conditions, e.g., burns, sepsis, or tuberculosis. In many cases the emergence of cachexia (a secondary condition) makes it difficult to continue appropriate therapy for the primary disease (cancer, HIV/AIDS etc.). A knowledge of impending cachexia would allow physicians to institute early measures to combat the condition and maintain body weight, thereby allowing continuation of therapy for the primary disease. Several detection assays can easily be developed, e.g., ELISA, RIA, and antibody-impregnated "dipsticks." Biological samples appropriate for such detection include serum, saliva, and urine. The antibodies used in the assays may be polyclonal or monoclonal.

EXAMPLE 15
Azaftig Use in Fat Reduction

Following an approved protocol, azaftig will be administered by peripheral routes to normalize body weight and reduce fat deposit in obese patients at risk for hypertension, cardiovascular diseases, diabetes and other ailments associated with obesity. This method of reducing fat deposit ('chemical liposuction') is much preferable over surgical removal of fat, which is not only expensive but it also poses serious risk of infection and surgical anesthesia.

EXAMPLE 16–18
Development of ELISA for Mac16 Glycoprotein

To further analyze differences between azaftig and MAC16, a polyclonal antibody against the octadecapeptide sequence of the protein core of MAC16 glycoprotein was generated. This antibody was then used in an enzyme-linked immunosorbent assay (ELISA) to test for the presence of MAC16 in the urine of cachectic patients, as described in D. Shiuan et al., "Competitive enzyme-linked immunosorbent assay for protein," Methods in Enzymology, vol. 279, pp. 321–26 (1997).

Generation of MAC 16 Peptide and ELISA Assay

A peptide was synthesized by Alpha Diagnostics, San Antonio, Tex. to match the reported sequence of the peptide core of MAC 16: $NH_2$-Tyr-Asp-Pro-Glu-Ala-Ala-Ser-Ala-Pro-Gly-Ser-Gly-Asp-Pro-Ser-His-Glu-Ala-Cys-COOH, as described by P. Todorov et al., "Characterization of a cancer cachectic factor," Nature, vol. 379, pp. 739–742 (1996). The purity of the synthesized peptides was determined by mass spectroscopy, high-pressure liquid chromatography, amino acid analysis, and amino acid sequence analysis. Goat anti-rabbit immunoglobulin G antibody (the second antibody), substrate, and all other reagents for ELISA were purchased from Alpha Diagnostic International, Inc., San Antonio, Tex., USA.

Production of polyclonal antibody

The synthesized peptide was coupled to keyhole limpet hemocyanin (KHL) using m-maleimidobenzoyl-N-hydroxysuccinimide ester (MBH) as the bifunctional agent. Two adult New Zealand rabbits received primary injection of peptide-KLH conjugate (0.3–0.4 mg/rabbit) emulsified in Freund's complete adjuvant. All injections were made at multiple sites by subcutaneous and intramuscular routes. Multiple booster injection was given with peptide-KLH conjugate (0.3–0.4 mg/rabbit) emulsified in Freund's incomplete adjuvant every two weeks. The first blood was drawn 1 week after the 5th injection, and the antibody titer was measured as described below. Thereafter, animals were injected with booster every two weeks and bled one week after each injection.

Procedure for competitive ELISA

The synthesized peptide (0.5 mg/ml) was diluted to 1.0 ug/ml in coating buffer consisting of 50 mM sodium phosphate, 145 mM NaCl, pH 7.4, and an antigen stabilizer. The wells of high-binding microtiter plates were coated with 0.1 ml of peptide (1.0 ug/ml) by overnight incubation at 4° C. All further operations were performed at room temperature (22–23° C.). To wash the wells of the microtiter plate or to remove its contents, the plate was rapidly inverted and the contents forcefully dashed into a tray. Each well was washed 3 times with 0.3 ml wash buffer (50 mM sodium phosphate, 145 mM NaCl, 0.05% Tween, 0.1% $NaN_3$, pH 7.4 containing an antigen stabilizer), blocked for 3 hr with 0.2 ml of blocking buffer (10% bovine serum albumin, 50 mM sodium phospate, 145 mM NaCl, pH 7.4, and an antigen stabilizer), and the buffer was then removed. To each well was added an unknown sample or control sample of increasing amounts of peptide in a total volume of 50 µl, 50 µl of the peptide-antibody diluted (1:400 to 1:6,400) in ELISA buffer (1.5% bovine serum albumin, goat/fetal bovine serum, 0.1% $NaN_3$, and an antigen stabilizer), and 150 µl of ELISA buffer. This solution was incubated for 3 hours. At the end of incubation, plates were washed 3 times with wash buffer, and 0.1 ml of goat anti-rabbit IgG conjugated with horseradish peroxidase (diluted 1:2000 in ELISA buffer) was added and incubation was continued for an additional 30 minutes. Plates were washed 5 times with wash buffer. The enzymatic reaction was initiated by addition of 0.1 ml of TMB substrate solution (50 mM tetramethylbenzidine, 1% dimethylsulfoxide, 0.01% hydrogen peroxide, and an antigen stabilizer). The reaction was terminated 15 min later by the addition of 0.1 ml of stop solution (0.2 M sulfuric acid in water). Absorbance was measured at 450 nm using an ELISA plate reader.

Immunoidentity Between MAC16 Glycoprotein and Synthetic Peptide

The reliability of the measurement of the endogenous level of MAC16 glycoprotein by ELISA in urine or other body fluids depends on the specificity of the antibody used. Using anti-peptide antibody, we have shown a close immunoidentity between urinary MAC 16 glycoprotein and the synthetic peptide. The addition of synthetic peptide to the assay well led to a dose-dependent decrease in the binding of peptide-antibody to the peptide attached to the well, and therefore to a decrease in $A_{450\ nm}$. (FIG. 15, closed circles) Under the conditions described above, the limit of detection was about 50 ng/ml or 1.0 ng per well. The useful range of the standard curve, however, extended up to 1000 ng/ml.

Figure 15:
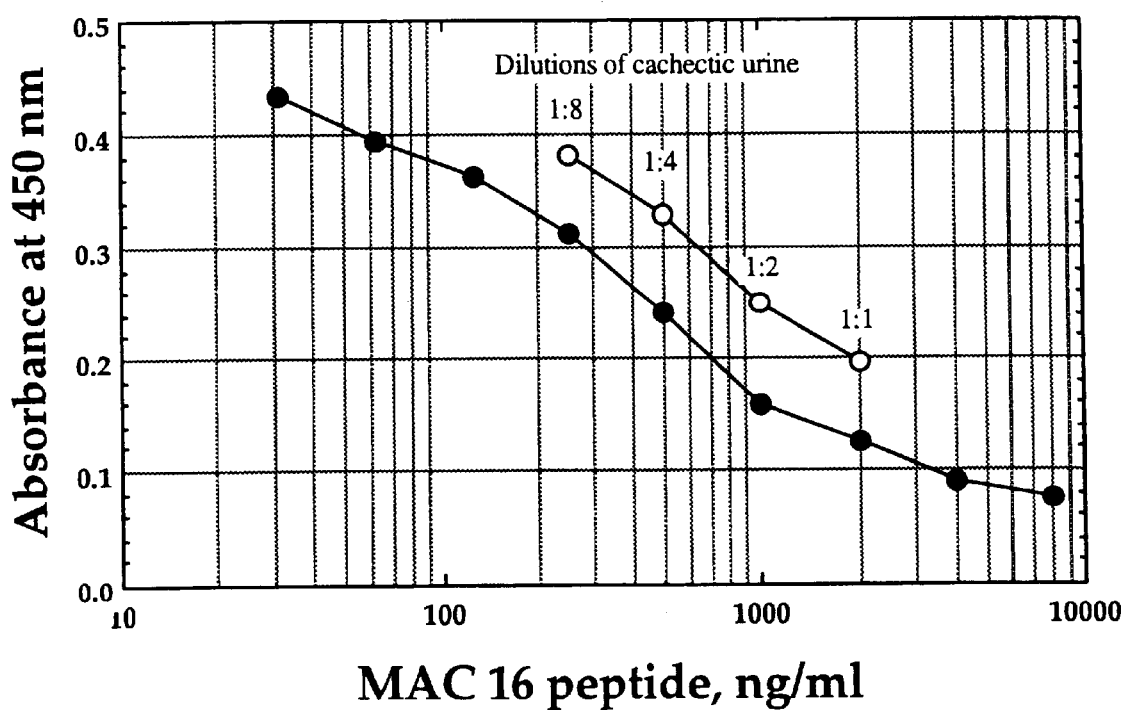
FIG. 15 illustrates the binding pattern of the synthetic peptide core of MAC16 and the MAC16 from urine of AIDS patients.

Urine samples were diluted twofold at a time (1:1 to 1:8), and 50 µl was used for ELISA. The ability of the synthetic peptide and MAC 16 in urine to inhibit antigen-antibody reaction in ELISA was compared. The addition of urine from a cachectic AIDS patient to the assay well reduced $A_{450\ mm}$ in proportion to its MAC 16 glycoprotein content in a manner parallel to the synthetic peptide (FIG. 15, open circles). These data suggest an immunoidentity between urinary MAC 16 glycoprotein-like immunoreactivity and synthetic peptide inmmunoreactivity.

Distribution of MAC16 Glycoprotein and Azaftig in Urine from AIDS Patients

Urine samples from 17 of the HIV-positive patients previously analyzed for the presence of azaftig by a Western Blot assay (Example 4 above), were now analyzed for the presence of MAC16 by ELISA. Urine from 12 of the patients showed detectable levels of the MAC-16 protein (>20 ng/ml) in the urine. However, there was no correlation (r=0.24, p=0.35) between the amount of urinary MAC-16 glycoprotein and weight loss. Azaftig did show a correlation with weight loss. Urine from six patients had detectable MAC-16 levels (>20 ng/ml) without detectable azaftig, and 3 patients without MAC-16 glycoprotein had azaftig.

Azaftig, combined with a pharmaceutically acceptable carrier, may be administered to mammals, including humans, intravenously, subcutaneously, percutaneously, intramuscularly, or intranasally to control weight loss.

The dosage will vary depending on the specific purpose for which azaftig is administered; appropriate dosages may readily be determined by those of skill in the art, an "effective amount" being that which increases (azaftig) weight loss by a statistically significant amount.

The complete disclosures of all references cited in this specification are hereby incorporated by reference. In the event of an otherwise irreconcilable conflict, however, the present specification shall control. Also incorporated by reference is the complete disclosure of the following two papers, which are not prior art to the present invention: J. Figueroa et al., "Azaftig, a urinary proteoglycan from cachectic cancer patients, causes profound weight loss in mice," submitted for publication in Life Sciences (1998); and J. Figueroa et al., "Abundance of a 24 KD proteoglycan in the urine of both cachectic AIDS and cachectic cancer patients," submitted for publication to AIDS Research and Human Retroviruses (1998).

We claim:

1. A substantially pure azaftig wherein said azaftig is a proteoglycan of molecular weight about 24 kDa as determined by sodium dodecyl sulfate-polyacrylamide gel electrophoresis; wherein said azaftig is obtained from or is identical to a proteoglycan obtained from urine of cachectic cancer patients; wherein said azaftig is a proteoglycan as determined by partial digestion with either chondroitinase ABC or chondroitinase AC; wherein said azaftig is not readily digested by neuraminidase; wherein said azaftig binds to fat cell membranes; wherein said azaftig does not bind to muscle cell membranes; and wherein said azaftig is a negatively charged molecule as determined by DEAE-Sephacel chromatography at pH 7.0.

2. A method for inducing weight loss in a mammal, comprising administering an effective amount of azaftig to the mammal; wherein azaftig is a proteoglycan of molecular weight about 24 kDa as determined by sodium dodecyl sulfate-polyacrylamide gel electrophoresis; wherein azaftig is obtained from or is identical to a proteoglycan obtained from urine of cachectic cancer patients; wherein azaftig is a proteoglycan as determined by partial digestion with either chondroitinase ABC or chondroitinase AC; wherein azaftig is not readily digested by neuraminidase; wherein said azaftig binds to fat cell membranes; wherein azaftig does not bind to muscle cell membranes; and wherein azaftig is a negatively charged molecule as determined by DEAE-Sephacel chromatography at pH 7.0.

3. The method of claim 2, wherein the mammal is a human.

* * * * *